United States Patent
Kim et al.

(10) Patent No.: US 8,827,918 B2
(45) Date of Patent: Sep. 9, 2014

(54) SYSTEM AND METHOD OF BALLISTOCARDIOGRAM-BASED PERSONAL AUTHENTICATION

(71) Applicant: Seoul National University R&DB Foundation, Seoul (KR)

(72) Inventors: Heechan Kim, Seoul (KR); Seungwoo Noh, Busan (KR); Chiyul Yoon, Gyeonggi-do (KR)

(73) Assignee: Seoul National University R&DB Foundation, Seoul (KR)

( * ) Notice: Subject to any disclaimer, the term of this patent is extended or adjusted under 35 U.S.C. 154(b) by 0 days.

(21) Appl. No.: 13/887,864

(22) Filed: May 6, 2013

(65) Prior Publication Data
US 2014/0142451 A1 May 22, 2014

(30) Foreign Application Priority Data
Nov. 16, 2012 (KR) .................. 10-2012-0130439

(51) Int. Cl.
- *A61B 5/02* (2006.01)
- *A61B 5/11* (2006.01)
- *G07C 9/00* (2006.01)
- *A61B 5/117* (2006.01)

(52) U.S. Cl.
CPC ............. *A61B 5/117* (2013.01); *A61B 5/1102* (2013.01); *G07C 9/00087* (2013.01); *G07C 9/00158* (2013.01)
USPC ........................................ 600/526; 340/5.53

(58) Field of Classification Search
CPC ...... A62B 5/029; A62B 5/028; A62B 5/1102; G07C 9/00087; G07C 9/00158
USPC ........................................ 600/526; 340/5.53
See application file for complete search history.

(56) References Cited

U.S. PATENT DOCUMENTS

| 2005/0124864 A1* | 6/2005 | Mack et al. ............ 600/300 |
| 2010/0090798 A1* | 4/2010 | Garcia Molina et al. .... 340/5.53 |
| 2012/0123279 A1* | 5/2012 | Brueser et al. ............ 600/481 |
| 2012/0189170 A1* | 7/2012 | Uno et al. ............ 382/115 |

FOREIGN PATENT DOCUMENTS

JP     2012-176106 A    9/2012

* cited by examiner

*Primary Examiner* — Christopher D Koharski
*Assistant Examiner* — Michael Carey
(74) *Attorney, Agent, or Firm* — The PL Law Group, PLLC (57) ABSTRACT

A ballistocardiogram-based personal authentication method includes detecting ballistocardiogram training signals of persons to be registered, extracting training features from the detected ballistocardiogram training signals, generating training data for personal authentication based on the extracted training features, detecting ballistocardiogram authentication signals of persons to be authenticated, and comparing the ballistocardiogram authentication signals and the training data to determine whether or not to perform the personal authentication of the persons to be authenticated. Thereby, the personal authentication method can perform personal authentication according to feature of a ballistocardiogram of each individual.

15 Claims, 5 Drawing Sheets

SYSTEM AND METHOD OF BALLISTOCARDIOGRAM-BASED PERSONAL AUTHENTICATION

CROSS REFERENCE TO RELATED APPLICATIONS AND CLAIM OF PRIORITY

This application claims priority to Korean Patent Application No. 10-2012-0130439, filed on Nov. 16, 2012, in the Korean Intellectual Property Office, the entire disclosure of which is incorporated herein by reference.

BACKGROUND

1. Field of the Invention

The present invention relates to a personal authentication system and method using a personal ballistocardiogram signal.

2. Description of the Related Art

With the development of forgery techniques, attention is being paid to person authentication modalities based on physiological instrumentation. This is because, unlike existing authentication modalities representative of a key and a password, it is difficult to forge physiological features peculiar to each individual. Representative examples of the physiological features which are peculiar to the individuals and which are used for personal authentication at present include a fingerprint, an iris, a hand dorsal vein, and so on.

Physiological signals other than the physical patterns such as the fingerprint, the iris, and the hand dorsal vein may also provide different features for each individual. For example, an electrocardiogram waveform based on a physiological structural difference of the heart which exists between individuals may be used for personal authentication. It is reported in various researches that individuals can be distinguished through a relative interval between characteristic points of the electrocardiogram waveform representative of a P wave, a QRS complex, and a T wave (PQRST), an amplitude ratio, or a specific combination of frequency components.

However, to measure the electrocardiogram, adhesive electrode pads should be attached to a human body. Attaching the electrode pads each time for the personal authentication gives rise to discomfort and aversion to an authenticating process. When many users are to be authenticated, this is accompanied with discomfort that the adhesive electrode pads should be frequently exchanged.

SUMMARY

Accordingly, the present invention has been made keeping in mind the above problems occurring in the related art, and the present invention is intended to propose a ballistocardiogram-based personal authentication system and method capable of identifying a specific person using a ballistocardiogram signal.

According to one aspect of the present invention, there is provided a ballistocardiogram-based personal authentication method, which includes:) detecting a ballistocardiogram training signal of a person to be registered; extracting a training feature from the detected ballistocardiogram training signal; generating training data for personal authentication based on the extracted training feature; detecting a ballistocardiogram authentication signal of a person to be authenticated; and comparing the ballistocardiogram authentication signal and the training data to determine an authentication of the person to be authenticated.

Here, the extraction of the training feature may include: extracting at least one period from each ballistocardiogram training signal; dividing the extracted period at regular intervals to select a plurality of feature extracting points; and calculating characteristic values of the plurality of feature extracting points.

Further, the characteristic values may include height values and slope values of the feature extracting points.

Also, the extraction of the training feature may further include converting the calculated characteristic values into vectors.

Further, the extraction of the training feature may apply a discrimination algorithm for classification into user individuals to the extracted training features, and generate the training data.

Also, the discrimination algorithm may maximize a ratio of scatter of feature data of the same person to a central distance between feature data of other persons among the extracted training features using linear discriminant analysis.

Further, the comparing may include: extracting authenticating features from the ballistocardiogram authentication signals; and applying the authenticating features to the training data to determine whether or not to perform the personal authentication.

In addition, the ballistocardiogram-based personal authentication method may further include additionally applying the ballistocardiogram authentication signal of the person to be authenticated to the training data to update the training data if the person to be authenticated is authenticated.

According to another aspect of the present invention, there is provided a ballistocardiogram-based personal authentication system, which includes: a piezoelectric element detecting a ballistocardiogram signal of a person to be authenticated; a feature extracting part extracting a feature from the ballistocardiogram signal; a data storing part storing training data generated based on the feature extracted from ballistocardiogram signals of a person to be registered; and an authentication processing part comparing the training data and the feature extracted by the feature extracting part and determining whether or not the person to be authenticated is matched with the person to be registered.

Here, the feature extracting part may include an amplifier amplifying the ballistocardiogram signals and a filter removing noises from the ballistocardiogram signals.

Further, the feature extracting part may extract at least one period from each ballistocardiogram signal, divides the extracted period at regular intervals to select a plurality of feature extracting points, and calculate characteristic values of the plurality of feature extracting points.

Also, the characteristic values may include height values and slope values of the feature extracting points.

Further, the feature extracting part may convert the calculated characteristic values into vectors.

Also, the training data for a plurality of persons to be registered may be generated by applying a discrimination algorithm for classifying the persons to be registered into individuals to the features extracted from the ballistocardiogram signals of the persons to be registered.

Further, the features extracted from the ballistocardiogram signals of the persons to be registered may be obtained by extracting at least one period from each ballistocardiogram signal, dividing the extracted period at regular intervals to select a plurality of feature extracting points, and converting characteristic values of the plurality of feature extracting points into vectors.

Also, the discrimination algorithm may maximize a ratio of scatter of feature data of the same person to a central distance between feature data of other persons using linear discriminant analysis.

Further, the ballistocardiogram-based personal authentication system may further include a data updating part that additionally applies the feature of the person to be authenticated by the authentication process part to the training data to update the training data if the person to be authenticated is authenticated.

Also, the piezoelectric element may include a plurality of piezoelectric elements installed apart from each other to detect ballistocardiograms of the person to be authenticated from a plurality of spots of a body of the person to be authenticated.

In addition, the plurality of piezoelectric elements may include a first piezoelectric element to detect a vertical component of the heart beat signal, and a second piezoelectric element to detect a horizontal component of the heart beat signal.

The ballistocardiogram-based personal authentication system and method detect a physical impact rather than an electric signal without an intentional touch of a body to a detecting device as in fingerprint or iris recognition, compared to an existing electrocardiogram-based personal authentication method, so that they can reliably detect a signal without being influenced by environmental variables such as a thickness of clothing or a degree of sweating.

Further, the ballistocardiogram-based personal authentication system and method still have advantages of a physiological recognition method compared to a traditional security device such as a key or a password, and do not require a touch to a device for each authentication unlike the physiological recognition method.

The technical effects of the present invention are not limited to the aforementioned effects, and other technical effects that are not mentioned may be definitely understood by the person skilled in the art from the following description.

BRIEF DESCRIPTION OF THE DRAWINGS

The above and other objects, features, and advantages of the present invention will be more clearly understood from the following detailed description when taken in conjunction with the accompanying drawings, in which.

DETAILED DESCRIPTION OF THE INVENTION

Reference will now be made in greater detail to embodiments of the invention with reference to the accompanying drawings. It should be understood that the present invention is not limited to the following embodiments and may be embodied in different ways. Thus, the embodiments are given to provide complete disclosure of the invention and to provide a thorough understanding of the invention to those skilled in the art. In the drawings, the sizes and shapes of elements may be exaggerated for clarity, and components denoted by like reference numerals refer to like components.

Figure 1:
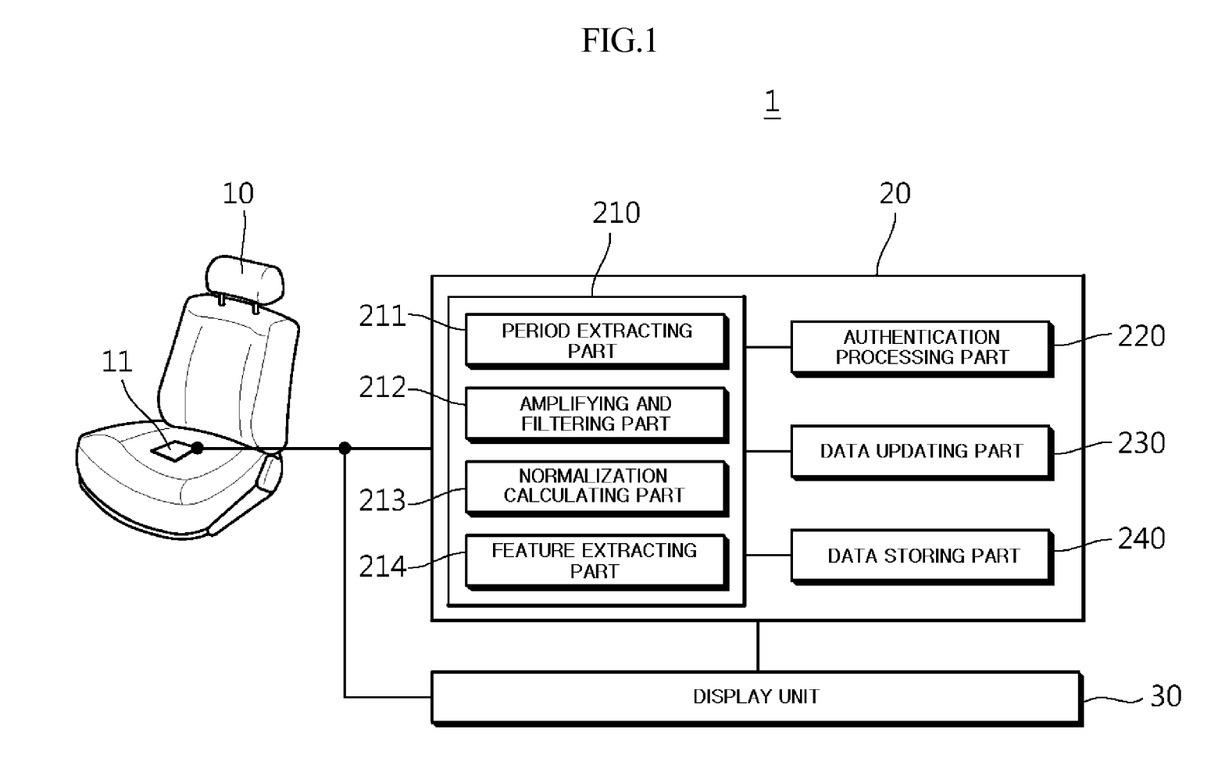
FIG. 1 shows a configuration of a personal authentication system according to a first embodiment of the present invention.

FIG. 1 shows a configuration of a personal authentication system according to a first embodiment of the present invention.

The personal authentication system 1 according to the first embodiment of the present invention may be used for both a case in which a person to be registered registers his/her own biomedical information with the personal authentication system, and a case in which a person to be authenticated performs an authentication procedure on the personal authentication system. In the following description, the person to be registered and the person to be authenticated are distinguished from one another, but they are called a person when they need not be distinguished from one another.

As shown in FIG. 1, the personal authentication system 1 according to the first embodiment of the present invention includes a seat member 10, a calculation unit 20, and a display unit 30.

The seat member 10 may be in the form of a seat which the person can take. The seat member 10 is equipped with a piezoelectric element 11.

As shown in FIG. 1, the piezoelectric element 11 may be installed on a portion on which the hips of the person are placed on the seat member 10 so as to be able to detect a heart beat of the person along with a load of the person which is applied in a vertical direction. Alternatively, the piezoelectric element 11 may be installed on a seat back of the seat member 10 so as to be able to detect the heart beat of the person along with a force transmitted when the person leans against the seat back.

The piezoelectric element 11 may output an external force, which is detected by the piezoelectric element 11, and an external force, which is changed by the heartbeat of the person, as electrical signals. Here, the electrical signals which the piezoelectric element 11 outputs may be voltage signals.

As shown in FIG. 1, the calculation unit 20 may include a feature checking part 210, an authentication processing part 220, a data storing part 240, and a data updating part 230, and be electrically connected with an output terminal of the piezoelectric element 11.

The feature checking part 210 may include a period extracting part 211, an amplifying and filtering part 212, a normalization calculating part 213, and a feature extracting part 214, and may check a feature based on a method as described below.

1. Period Extraction

The period extracting part 211 may receive the signal detected by the piezoelectric element 11, and extract at least one period from the signal. The period extracted by the period extracting part 211 may be based on a ballistocardiogram of the person.

Figure 2:
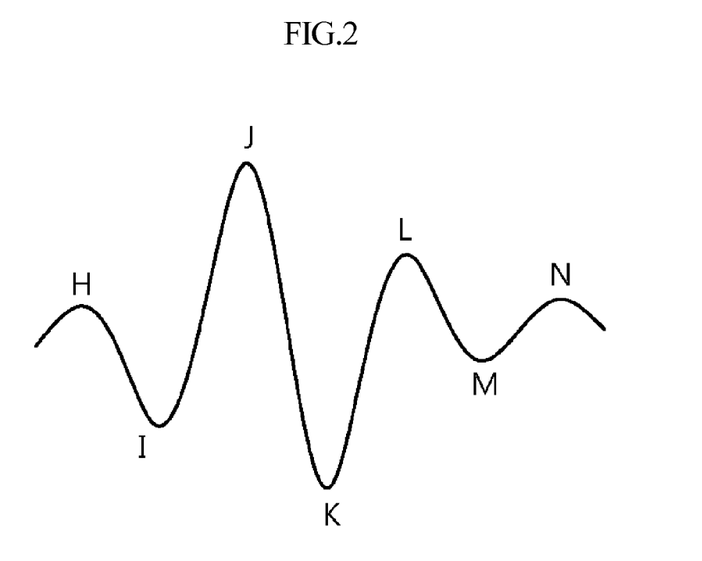
FIG. 2 shows a representative one-period graph of a ballistocardiogram.

FIG. 2 is a graph showing one period representative of a ballistocardiogram.

As shown in FIG. 2, a general ballistocardiogram has a waveform indicated by different waves of H, I, J, K, L, M, and N waves. The H wave takes place when the right/left ventricle begins to contract, and the I wave takes place in reaction to the H wave. Thereafter, when a stream of blood is pushed from the left ventricle to an aortic arch, the J wave takes place. The K wave takes place due to deceleration of the blood stream flowing from the left ventricle to the aortic arch. Then, a pressure of the left ventricle begins to be lower than that of the aortic arch, and an aortic valve is closed. Further, a pressure of the right ventricle begins to be lower than that of a pulmonary artery, and a pulmonary valve is closed. In this case, when the aortic valve and the pulmonary valve begin to close, the L wave takes place. Then, when an atrium begins to relax, the M wave takes place. When the blood stream reversely flowing when the left and right atria are again filled with blood begins to be obstructed by a tricuspid valve and a mitral valve, the N wave takes place.

However, unlike an electrocardiogram, the ballistocardiogram actually has an indefinite specific point and a great difference between personal waveforms. As such, it is difficult to use an existing period detection algorithm for the ballistocardiogram.

Thus, i) it is possible to acquire a heart beat period from the ballistocardiogram signal on the basis of another signal generated in synchronization with the heart beat, for instance an electrocardiogram signal, a phonocardiogram signal, or a photoplethysmogram signal, or ii) it is possible to compare the acquired heart beat signal with a representative heart beat signal to acquire a signal between two continuously detected peak points as one period.

The period extracting part 211 may extract at least one heart beat period of the person from the signal detected by the piezoelectric element 11 using the method i) or ii).

Further, the period extracting part 211 may be configured to sample an analog signal detected by the piezoelectric element 11, to convert the sampled analog signal into a digital signal, and then to extract a period from the digital signal.

2. Amplifying and Filtering of Signal

The amplifying and filtering part 212 may amplify a signal corresponding to one period extracted by the period extracting part 211. Further, the amplifying and filtering part 212 may transmit only a signal of a frequency band of the ballistocardiogram signal among the amplified signal, and attenuate and remove signals of the other frequency bands as noises. For example, such noises may be removed using a high pass filter that transmits 10 KHz or more signals.

Further, the amplifying and filtering part 212 may be configured to receive the signal corresponding to one period from the period extracting part 211 first, to attenuate and remove noises from the signal, and to amplify the filtered signal.

3. Normalization

The normalization calculating part 213 may receive the signal processed by the amplification and filtering from the amplifying and filtering part 212, and normalize longitudinal and transverse axes of the signal.

The persons are different in heart beat period and heart beat intensity from each other. Even in the case of the same person, the heart beat period and the heart beat intensity differ according to circumstances. Thus, to compare data having different heart beat periods and intensities, it is necessary to normalize the longitudinal axis (corresponding to the heart beat period) of the signal and transverse axis (corresponding to the heart beat intensity) of the signal.

Thus, the normalization calculating part 213 may normalize each of the longitudinal and transverse axes of the signal with a predetermined criterion in order to minimize a time-varying influence of the heart beat. For example, the longitudinal axis corresponding to the heart beat period may be normalized by sampling of a unit of 1 k per period, and the transverse axis corresponding to the heart beat intensity may be normalized by standard scoring. Details of a standardized algorithm are apparent to those skilled in the art, and thus will be omitted.

4. Feature Extraction

Figure 3:
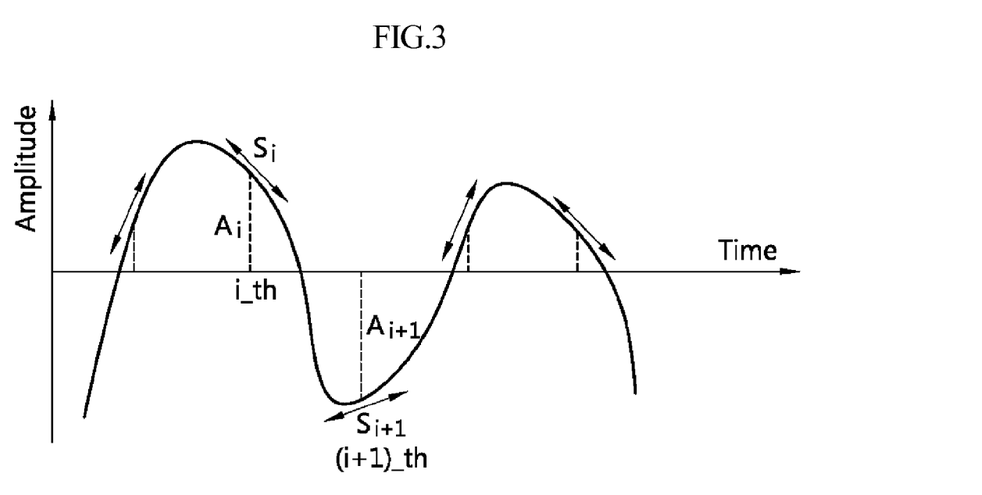
FIG. 3 shows an example of extracting a feature from the ballistocardiogram.

The feature extracting part 214 may extract a feature of the person from the signal normalized by the normalization calculating part 213. FIG. 3 shows an example of feature extraction from the ballistocardiogram.

As shown in FIG. 3, the feature extracting part 214 may select N feature extracting points by dividing the ballistocardiogram signal of one period at regular intervals on the basis of a time axis (transverse axis), and extract a height value and a tangential slope value at each feature extracting point as a feature. The extracted feature can be expressed by one-dimensional vector as follows.

$$f_i = (A_i, S_i, A_{i+1}, S_{i+1}, \ldots, A_{i+N-1}, S_{i+N-1})$$ [Equation 1]

Further, when the features are extracted above one period by the feature extracting part 214, the features of the person can be expressed by a sample matrix as follows.

$$X = \begin{vmatrix} A_1 & A_{N11} & \ldots & A_{(M-1)\times N11} \\ S_1 & S_{N11} & \ldots & A_{(M-1)\times N11} \\ A_2 & A_{N12} & \ldots & A_{(M-1)\times N12} \\ S_2 & S_{N12} & \ldots & S_{(M-1)\times N12} \\ \vdots & \vdots & \vdots & \vdots \\ A_N & A_{2N} & \ldots & A_{M\times N} \\ S_N & S_{2N} & \ldots & S_{M\times N} \end{vmatrix}$$ [Equation 2]

5. Linear Discriminant Analysis

To distinguish and authenticate the persons, the feature extracting part 214 may process the sample matrix using a linear discriminant analysis (LDA).

LDA is a technique that calculates an optimal linear discriminant function so as to be able to map data to a specified space to check a class. In detail, in a multidimensional space in which the features extracted from the persons coexist, the extracted features are mapped to a low-dimensional space in which the persons are distinguished from one another. Thereby, the persons can be distinguished and authenticated.

A projected sample matrix can be expressed as follows.

$$Y = W^T X$$ [Equation 3]

Here, W is a transformation matrix that transforms the sample matrix X into the projected sample matrix Y.

The transformation matrix W is selected so that a ratio of between-class scatter to within-class scatter is maximized. This can be expressed by the following equation.

$$J(W) = \frac{|\tilde{S}_B|}{|\tilde{S}_W|} = W^T X \frac{|W^T S_B W|}{|W^T S_W W|}$$ [Equation 4]

Here, $S_B$ is a between-class-scatter matrix and $S_W$ is a within-class-scatter matrix.

The transformation matrix W may be selected so that an objective function J(W) has a maximum value.

The sample matrix X can be processed into training data through the aforementioned processes.

Meanwhile, the data storing part 240 may store information about the persons to be registered, information about the ballistocardiogram signals of the persons to be registered, information about the features acquired from the ballistocardiogram signals, information about the training data, and so on.

The authentication processing part 220 may cause the feature acquired from the ballistocardiogram of the person to be authenticated to correspond to the training data generated from the features of the persons to be registered which are stored in the data storing part 240, and determine whether or not the person to be authenticated is matched with one of the persons to be registered.

With the passage of time, physiological signals of the human being may be gradually changed. Accordingly, when the personal authentication is carried out on the basis of the data measured previously, after a predetermined time has elapsed, a difference between the data stored in the system and the measured data is generated so that an authentication rate may be remarkably lowered.

Thus, the personal authentication system 1 according to the first embodiment of the present invention includes the data updating part 230 that can make up for this problem.

When it is determined by the authentication processing part 220 that the person to be authenticated is the person to be registered, the data updating part 230 may update the training data in such a manner that the feature extracted from the ballistocardiogram signal of the person to be authenticated is included in the training data of the corresponding person.

Alternatively, when it is determined by the authentication processing part 220 that the person to be authenticated is the person to be registered, the data updating part 230 allows the feature extracting part 214 to update the training data in such a manner that the feature extracted from the ballistocardiogram signal of the person to be authenticated is included in the training data of the corresponding person.

In this way, the data updating part 230 can continuously collect the features of the persons to be registered, maintain newest training data, and sustain an accurately authenticated state for the persons regardless of the passage of time.

Meanwhile, the display unit 30 may be connected with the piezoelectric element 11, and display a state of an external force applied to the piezoelectric element 11 through an electric signal output from the piezoelectric element 11. Alternatively, the display unit 30 may be connected with the calculation unit 20, and display a result of the authentication of the person to be authenticated.

Figure 4:
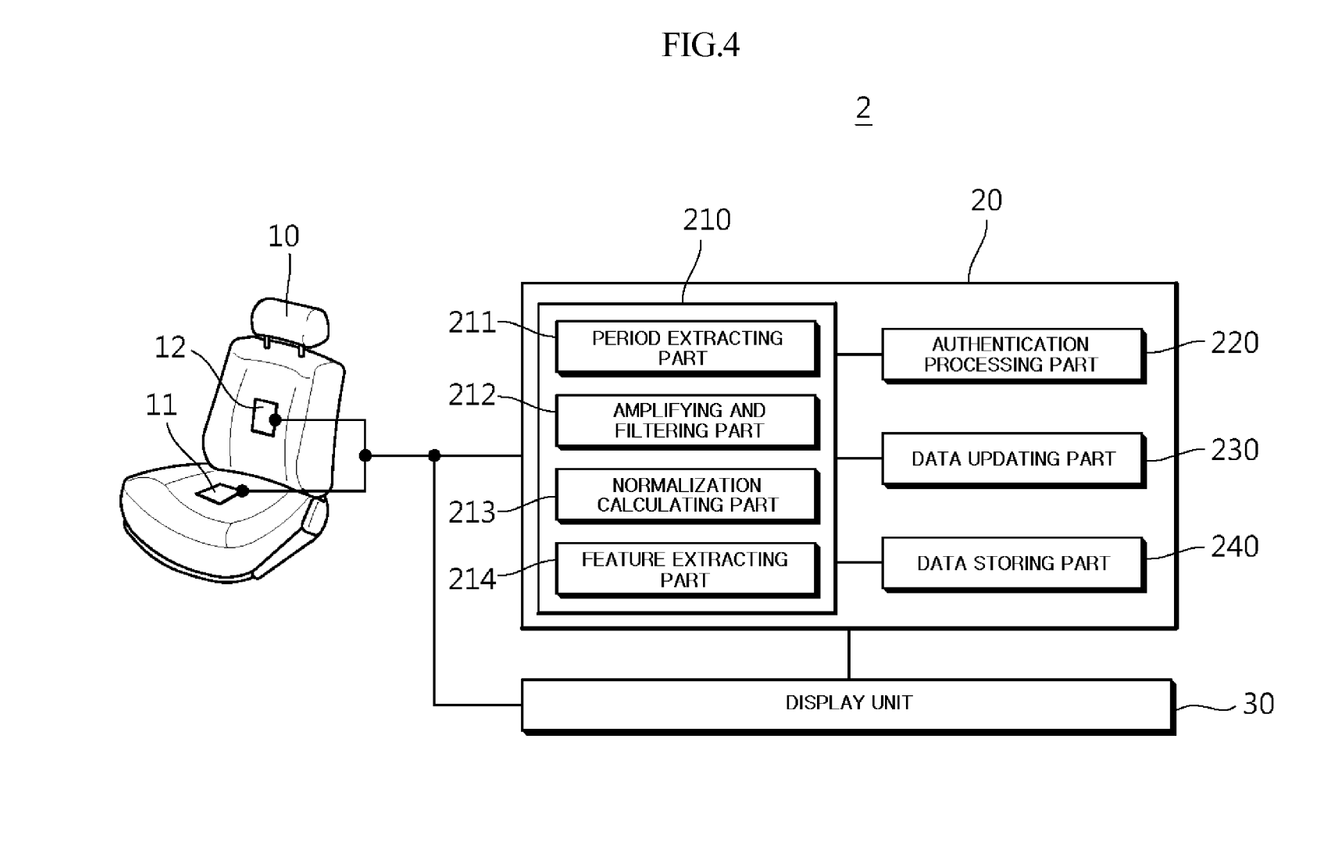
FIG. 4 shows a configuration of a personal authentication system according to a second embodiment of the present invention.

Hereinafter, a personal authentication system according to a second embodiment of the present invention will be described. For the convenience of description, components similar to those in the first embodiment will be designated by the same reference numerals, and components common to those in the first embodiment will not be described.

FIG. 4 shows a configuration of a personal authentication system according to a second embodiment of the present invention. In comparison with the personal authentication system 1 according to the first embodiment of the present invention, the personal authentication system 2 according to the second embodiment of the present invention has a difference in that at least two piezoelectric elements 11 and 12 may be installed on the seat member 10.

As shown in FIG. 4, the piezoelectric elements 11 and 12 of the personal authentication system 2 according to the second embodiment of the present invention may be installed on a portion on which the hips of a person are placed on the seat member 10 and a seat back of the seat member 10.

The piezoelectric element 11 installed on the portion on which the hips of the person are placed may detect a heart beat of the person which is applied in a vertical direction, and the piezoelectric element 12 installed on the seat back of the seat member 10 may detect a heartbeat of the person which is applied in a horizontal direction.

The ballistocardiogram is used to record vibrations generated when blood ejection caused by motion of the heart applies a mechanical impact to a human body. Since the vibrations generated by the blood ejection are applied in three dimensions, vertical vibrations and horizontal vibrations can be detected. Further, since the vertical and horizontal vibration patterns may show a minute difference between individuals, they are analyzed at the same time, so that authentication accuracy of the person can be improved.

To this end, the calculation unit 20 may process a signal obtained from the piezoelectric element 11 detecting the vertical vibrations and a signal obtained from the piezoelectric element 12 detecting the horizontal vibrations, and generate training data including both pieces of information.

Hereinafter, a personal authentication method using the personal authentication system 1 or 2 according to the embodiment of the present invention will be described.

Figure 5:
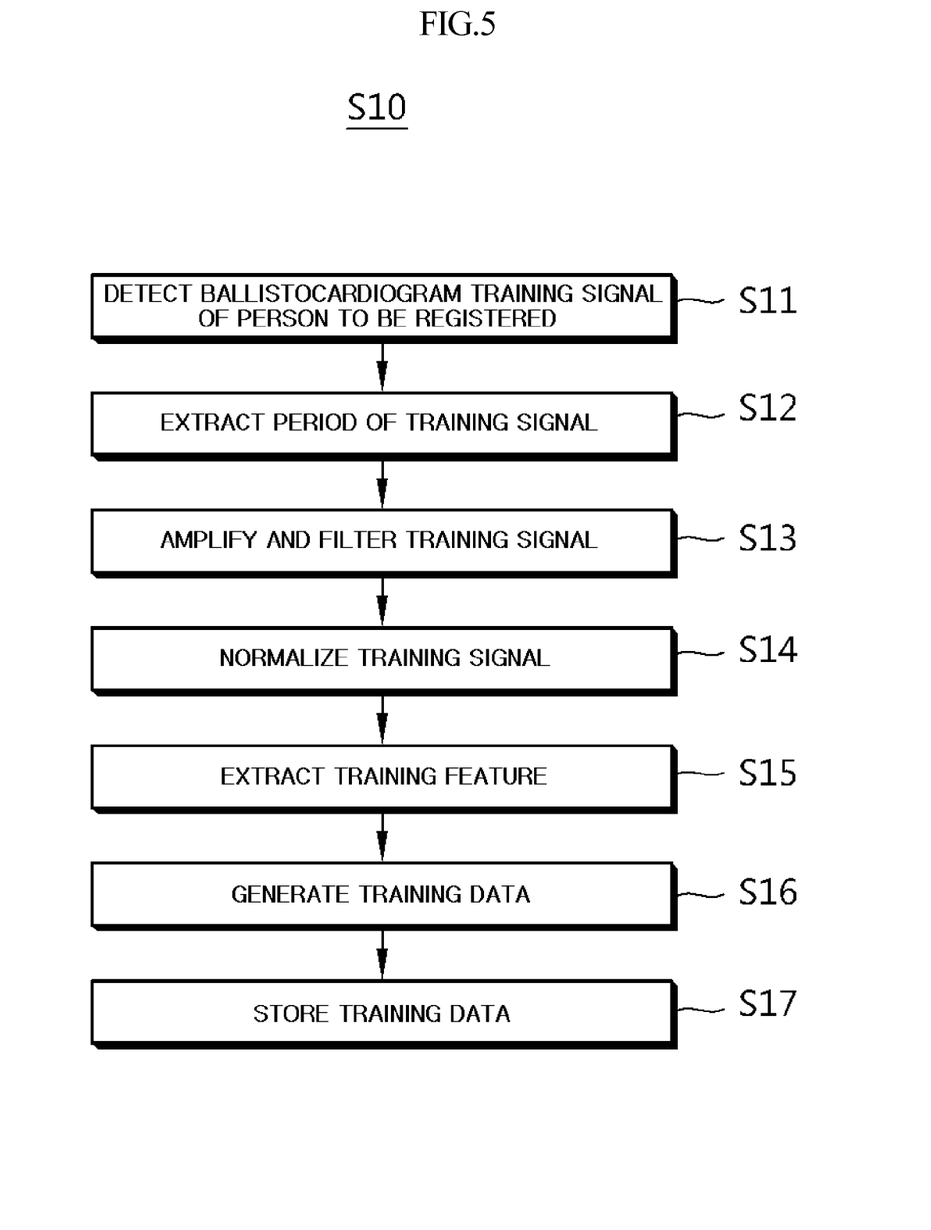
FIG. 5 is a flowchart showing a process of generating training data in a personal authentication method according to an embodiment of the present invention.
Figure 6:
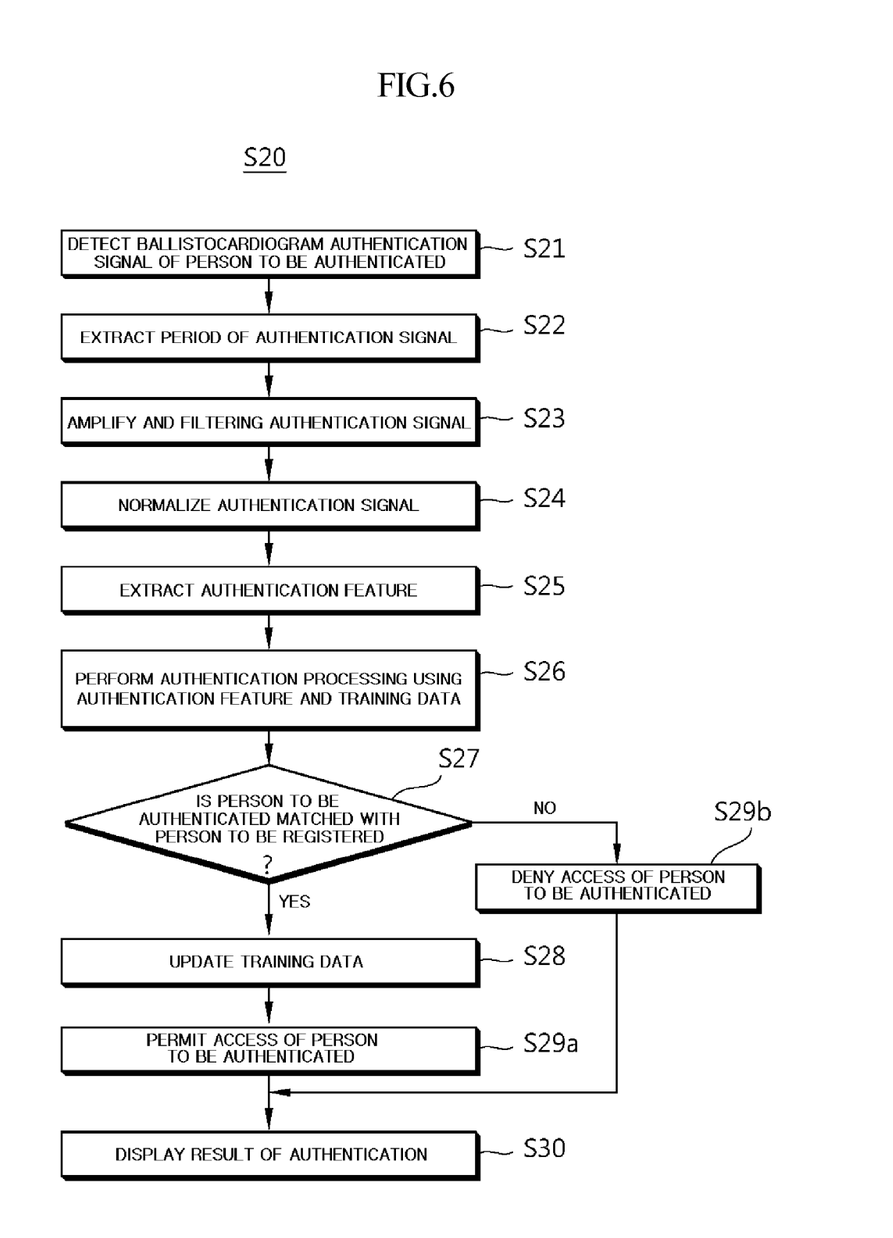
FIG. 6 is a flowchart showing a process of authenticating a person to be authenticated in the personal authentication method according to the embodiment of the present invention.

FIG. 5 is a flowchart showing a process of generating training data in a personal authentication method according to an embodiment of the present invention, and FIG. 6 is a flowchart showing a process of authenticating a person to be authenticated in the personal authentication method according to the embodiment of the present invention.

As shown in FIGS. 5 and 6, the personal authentication method according to the embodiment of the present invention includes a process S10 of generating training data, and a process S20 of authenticating a person to be authenticated.

As shown in FIG. 5, the process S10 of generating training data of the person to be registered may include a process S11 of detecting a ballistocardiogram training signal, a process S12 of extracting a period from the training signal, a process S13 of amplifying and filtering the training signal, a process S14 of normalizing the training signal, a process S15 of extracting a training feature, a process S16 of generating training data, and a process S17 of storing the training data.

In the process S11 of detecting the ballistocardiogram training signal, the person to be registered sits on the seat member 10, and the heart beat of the person to be registered is detected as the training signal by the piezoelectric element 11 installed on the seat member 10. The piezoelectric element 11 may detect vibrations caused by forces of vertical and/or horizontal components of the heart beat of the person to be registered according to a position at which it is installed on the seat member 10, and output the detected vibrations as an electric signal.

In the process S12 of extracting the period from the training signal, the period extracting part 211 may extract at least one of the heart beat periods of the person to be registered from the training signal converted into the electric signal by the piezoelectric element 11.

The period extracting part 211 may extract the heart beat period of the person to be registered from the training signal on the basis of another signal generated in synchronization with the heart beat, for instance, an electrocardiogram signal, a phonocardiogram signal, or a photoplethysmogram signal, or compare the training signal with the representative ballistocardiogram period to acquire a signal between two continuously detected peak points as one period. Further, in the period extracting process, the period extracting part 211 may sample an analog training signal detected by the piezoelectric element 11, convert the sampled analog training signal into a digital training signal, and extract the period from the digital training signal.

In the process S13 of amplifying and filtering the training signal, the signal corresponding to one period extracted by the period extracting part 211 may be amplified, only a signal of a frequency band corresponding to the ballistocardiogram signal may be transmitted, and signals of the other frequency bands may be attenuated and removed as noises. A band pass filter, a high pass filter, or a low pass filter may be used for filtering. However, to acquire the ballistocardiogram signal, the high pass filter transmitting signals of 10 KHz or more may be used. An order of the amplifying and the filtering may be reversed.

Further, the process S12 of extracting the period from the training signal and the process S13 of amplifying and filtering the training signal may also be reversed.

In the process S14 of normalizing the training signal, the normalization calculating part 213 normalizes the heart beat period and intensity with respect to the ballistocardiogram signal in which the period extraction and amplifying and filtering of the training signal are completed.

When a plurality of persons to be registered exist, the persons are different in heart beat period and intensity from each other. Even in the case of the same person to be registered, the heart beat period and intensity differ according to circumstances. Thus, to compare a plurality of data having different heart beat periods and intensities, it is necessary to normalize the heart beat period and intensity of each data, and then to compare the heart beat periods and intensities.

Thus, the normalization calculating part 213 may normalize each of the longitudinal and transverse axes of the signal with a predetermined criterion in order to minimize a time-varying influence of the heart beat. For example, the longitudinal axis corresponding to the heart beat period may be normalized by sampling of a unit of 1 k per period, and the transverse axis corresponding to the heart beat intensity may be normalized by standard scoring. Details of a standardized algorithm are apparent to those skilled in the art, and thus will be omitted.

In the process S15 of extracting the training feature, the feature extracting part 214 may select N feature extracting points by dividing the ballistocardiogram signal of one period at regular intervals on the basis of a time axis (transverse axis) with respect to the data in which the normalization of the heart beat period and intensity is completed by the normalization calculating part 213, extract a height value and a tangential slope value at each feature extracting point as a feature, and expresses the feature as a one-dimensional vector (see Equation 1).

Further, when the feature extracting part 214 extracts the features above one period with respect to one person to be registered, a sample matrix may be generated on the basis of the one-dimensional vector extracted from each period (see Equation 2).

In the process S16 of generating the training data, the feature extracting part 214 may generate the training data, by which the persons to be registered are distinguished from one another using linear discriminant analysis (LDA) on the basis of the sample matrix which is extracted for each person to be registered by the feature extracting part 214.

The feature extracting part 214 may generate the training data by selecting a transformation matrix W that can map the features extracted from the persons to be registered who coexist in a multidimensional space to a low-dimensional space in which the persons to be registered are distinguished from one another using the LDA. Thereby, the persons can be distinguished and authenticated. In this case, the transformation matrix W may be selected so that a ratio of between-class scatter to within-class scatter is maximized (see Equations 3 and 4).

In the process S17 of storing the training data, the training data generated on the basis of the features extracted from the persons to be registered may be stored in the data storing part 240. In this case, the data storing part 240 may store information about the persons to be registered, information about the ballistocardiogram signals of the persons to be registered, and information about the features acquired from the ballistocardiogram signals, in addition to the training data.

Meanwhile, as shown in FIG. 6, the process S20 of authenticating the person to be authenticated may include a process S21 of detecting a ballistocardiogram authentication signal, a process S22 of extracting a period from the authentication signal, a process S23 of amplifying and filtering the authentication signal, a process S24 of normalizing the authentication signal, a process S25 of extracting an authentication feature, a process S26 of processing authentication, a process S28 of updating training data, and a process S30 of displaying a result of the authentication.

The process S21 of detecting the ballistocardiogram authentication signal, a process S22 of extracting a period from the authentication signal, the process S23 of amplifying and filtering the authentication signal, the process S24 of normalizing the authentication signal, and the process S25 of extracting the authentication feature are similar to the aforementioned process S10 of generating the training data of the person to be registered, except that the person to be authenticated is set to a target for authentication, and detailed description thereof will be omitted.

In the process S26 of processing the authentication, the authentication processing part 220 causes the feature acquired from the ballistocardiogram of the person to be authenticated to correspond to the training data stored in the data storing part 240.

The feature of the person to be authenticated is applied to the training data. Thereby, the feature of the person to be authenticated is mapped to the low-dimensional space in which the persons to be registered are distinguished from one another, and it may be determined whether or not the person to be authenticated is matched with a class of any one of the persons to be registered (S27).

When the person to be authenticated is matched with any one of the persons to be registered, the process S28 of updating the training data may be advanced.

In the process S28 of updating the training data, the data updating part 230 may update the training data including the feature of the person to be authenticated who is recognized as the person to be registered in the training data of the person to be registered. Alternatively, the data updating part 230 may cause the feature extracting part 214 to update the training data including the feature of the person to be authenticated in the training data of the person to be registered.

This is intended to continuously collect the feature of the person to be registered to maintain newest training data, because physiological signals of the human being may be gradually changed with the passage of time, and when the personal authentication is carried out on the basis of the data measured previously, a difference between the data stored in the system and the measured data is generated after a predetermined time has elapsed, so that an authentication rate can be remarkably lowered.

Further, when the person to be authenticated is matched with any one of the persons to be registered, the person to be authenticated is allowed to access a system along with the process S28 of updating the training data (S29a).

In contrast, when the person to be authenticated is not matched with any one of the persons to be registered, the person to be authenticated is denied access to the system (S29b).

Simultaneously, in the process S30 of displaying the result of the authentication, the display unit 30 may display a result of the personal authentication of the person to be authenticated.

The ballistocardiogram-based personal authentication system and method as described above apply the ballistocardiogram, which is one of physiological signals, to personal authentication rather than disease diagnosis. As such, the personal authentication is possible merely by the act of a user sitting on the seat member without an intentional touch of the body to a separate device such as a fingerprint recognition device. Thus, the ballistocardiogram-based personal authentication system and method provide high applicability in various fields in which easy frequent personal authentication is required.

Particularly, since a user can be identified and distinguished merely by sitting on the seat member, the ballistocardiogram-based personal authentication system and method according to the present invention can be applied to a seat for a vehicle, authority to use the vehicle can be checked, and settings (e.g., a height and angle of the seat, adjustment of interior and side mirrors, adjustment of steering and suspension systems, adjustment of an airbag, etc.) for travelling in the vehicle according to the user can be automatically adjusted.

Further, the ballistocardiogram-based personal authentication system and method according to the present invention can be applied to security of an office environment, so that a user is checked against identity and authority to use a computer merely by sitting on the seat member, and is permitted to use the computer. Otherwise, the system is allowed to determine whether or not it permits a user to read documents according to authority of the user to read the documents.

In addition, the ballistocardiogram-based personal authentication system and method according to the present invention can be applied to a home health care field, so that which one of constituent family members measurements from various environment sensors lying sporadically at a bed, a sofa, a toilet seat, and so on belong to can be determined by ballistocardiogram waveforms when the measurements are taken, and be transmitted to a hospital management network.

Although embodiments of the present invention have been described for illustrative purposes, those skilled in the art will appreciate that various modifications, additions and substitutions are possible, without departing from the scope and spirit of the invention as disclosed in the accompanying claims.

What is claimed is:

1. A method for ballistocardiogram-based personal authentication, comprising:
    detecting a ballistocardiogram training signal of a person to be registered;
    extracting a training feature from the detected ballistocardiogram training signal;
    generating training data for personal authentication, based on the extracted training feature;
    detecting a ballistocardiogram authentication signal of a person to be authenticated; and
    comparing the ballistocardiogram authentication signal and the training data to determine an authentication of the person to be authenticated,
    wherein the extraction of the training feature includes:
    extracting at least one period from each ballistocardiogram training signal;
    dividing the extracted period at regular intervals to select a plurality of feature extracting points; and
    calculating characteristic values of the plurality of feature extracting points,
    wherein the characteristic values include height values and slope values of the feature extracting points.

2. The method according to claim 1, wherein the extraction of the training feature further includes converting the calculated characteristic values into vectors.

3. The method according to claim 1, wherein the generation of the training data comprises applying a discrimination algorithm for classification into user individuals to the extracted training features, and generating the training data.

4. The method according to claim 3, wherein the discrimination algorithm maximizes a ratio of scatter of feature data of the same person to a central distance between feature data of other persons among the extracted training features using linear discriminant analysis.

5. The method according to claim 1, wherein the comparing includes:
    extracting an authenticating feature from the ballistocardiogram authentication signal; and
    applying the authenticating feature to the training data to determine the authentication of the person to be authenticated.

6. The method according to claim 1, further comprising additionally applying the ballistocardiogram authentication signal of the person to be authenticated to the training data to update the training data if the person to be authenticated is authenticated.

7. A system for ballistocardiogram-based personal authentication, comprising:
    a piezoelectric element detecting a ballistocardiogram signal of a person to be authenticated;
    a feature extracting part extracting a feature from the ballistocardiogram signal;
    a data storing part storing training data generated based on the feature extracted from ballistocardiogram signal of a person to be registered; and
    an authentication processing part comparing the training data and the feature extracted by the feature extracting part and determining whether or not the person to be authenticated is matched with the person to be registered,
    wherein the feature extracting part extracts at least one period from each ballistocardio gram signal, divides the extracted period at regular intervals to select a plurality of feature extracting points, and calculates characteristic values of the plurality of feature extracting points, and
    wherein the characteristic values include height values and slope values of the feature extracting points.

8. The system according to claim 7, wherein the feature extracting part includes an amplifier amplifying the ballistocardiogram signal and a filter removing noises from the ballistocardiogram signal.

9. The system according to claim 7, wherein the feature extracting part converts the calculated characteristic values into vectors.

10. The system according to claim 7, wherein the training data for a plurality of persons to be registered is generated by applying a discrimination algorithm for classifying the persons to be registered into individuals to the features extracted from the ballistocardiogram signals of the persons to be registered.

11. The system according to claim 10, wherein the features extracted from the ballistocardiogram signals of the persons to be registered are obtained by extracting at least one period from each ballistocardiogram signal, dividing the extracted period at regular intervals to select a plurality of feature extracting points, and converting characteristic values of the plurality of feature extracting points into vectors.

12. The system according to claim 10, wherein the discrimination algorithm maximizes a ratio of scatter of feature data of the same person to a central distance between feature data of other persons using linear discriminant analysis.

13. The system according to claim 7, further comprising a data updating part that additionally applies the feature of the person to be authenticated by the authentication process part to the training data to update the training data if the person to be authenticated is authenticated.

14. The system according to claim 7, wherein the piezoelectric element comprises a plurality of piezoelectric elements installed apart from each other to detect ballistocardiograms of the person to be authenticated from a plurality of spots of a body of the person to be authenticated.

15. The system according to claim 14, wherein the plurality of piezoelectric elements comprises a first piezoelectric element to detect a vertical component of the heart beat signal, and a second piezoelectric element to detect a horizontal component of the heart beat signal.

* * * * *